(12) United States Patent
Carroll, Jr.

(10) Patent No.: US 6,230,547 B1
(45) Date of Patent: May 15, 2001

(54) TECHNIQUE FOR FREE-BLOWING PLASTIC PREFORMS

(75) Inventor: Max Lamar Carroll, Jr., Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/175,689

(22) Filed: Oct. 20, 1998

Related U.S. Application Data
(60) Provisional application No. 60/067,471, filed on Dec. 5, 1997.

(51) Int. Cl.[7] .................................................. G01N 3/18
(52) U.S. Cl. .................................................. 73/37; 73/788
(58) Field of Search ........................... 73/766, 788, 826, 73/37

(56) References Cited

U.S. PATENT DOCUMENTS

| | | |
|---|---|---|
| 3,916,673 | 11/1975 | Gass et al. . |
| 4,090,394 | 5/1978 | Herman et al. . |
| 4,139,586 | 2/1979 | Gasson . |
| 4,466,845 | 8/1984 | Fortune . |
| 5,017,325 | 5/1991 | Jackowski et al. . |
| 5,254,298 | 10/1993 | Ibar . |
| 5,326,393 | 7/1994 | Ibar . |
| 5,365,792 | 11/1994 | Carroll, Jr. . |
| 5,438,878 | 8/1995 | Carroll, Jr. . |
| 5,468,443 | 11/1995 | Takada et al. . |
| 5,509,796 | 4/1996 | Settembrini . |
| 5,611,987 | 3/1997 | Kato et al. . |

FOREIGN PATENT DOCUMENTS

| | | |
|---|---|---|
| 0 274 316 A1 | 7/1988 | (EP) . |
| 0 501 738 A2 | 9/1992 | (EP) . |

*Primary Examiner*—Max Noori
(74) *Attorney, Agent, or Firm*—Karen A. Harding; Harry J. Gwinnell

(57) ABSTRACT

A method and apparatus for determining the stretching characteristics of a polymer composition suitable for use in manufacturing a thermoplastic article, such as a bottle and preferably a bottle having PET, PEN and mixtures thereof, are provided. The method includes the steps of heating a bottle preform of the polymer composition to at least its glass transition temperature then free-blowing the preform in a manner so that the inflation pressure is varied inversely relative to the expansion of the article during at least a portion of the inflation step. An apparatus for free-blowing the thermoplastic articles in accordance with the method is also disclosed.

21 Claims, 5 Drawing Sheets

TECHNIQUE FOR FREE-BLOWING PLASTIC PREFORMS

CROSS-REFERENCE TO RELATED APPLICATIONS

Benefit is claimed to the earlier filed provisional application having U.S. Ser. No. 60/067,471 filed Dec. 5, 1997, the entire disclosure of which is incorporated herein by reference.

FIELD OF THE INVENTION

This invention relates to a process for determining the expansion characteristics of a thermoplastic suitable for use in forming a container and more particularly a bottle. In particular, the present invention relates to a process for free-blowing a thermoplastic bottle. More particularly, this invention relates to a method of using pressure variation in forming a free-blown, thermoplastic preform to determine the natural stretch ratio (NSR) of a thermoplastic polymeric composition. The present invention further relates to an apparatus for varying the inflation pressure exerted on the expanding preform during the free-blowing process.

BACKGROUND OF THE INVENTION

A great deal of interest has developed in producing biaxial oriented thermoplastic bottles having barrier properties and strength characteristics which make them attractive packaging containers for carbonated soft drink beverage containers as well as producing new thermoplastic compositions suitable for other beverages currently bottled in metal and/or glass containers. It will be readily appreciated that the functionality of such containers can be affected by numerous factors especially in the carbonated drink industry where a small volume increase will cause the gas to migrate from the beverage to the non-liquid space causing a deterioration in the quality of the product.

When producing beverage bottles from polymer compositions such as polyethylene terephthalate (PET) and poly (ethylene-2,6-naphthalene dicarboxylate), (PEN), copolymers or blends thereof, it is important that the polymer be well oriented during stretching. Proper orientation results in uniform material distribution in most areas of the bottle. Free-blowing of thermoplastics, particularly for PET and PEN, is a well known technique used to obtain empirical data on the stretching characteristics of a particular thermoplastic formulation. As used herein the term "free-blowing" or "free-blown" means that a preformed article is blow-molded without using a metal mold to obtain a secondary molded article and is analogous to blowing a rubber balloon. Such data desirably includes hoop and axial stretch ratios as well as other physical properties of the thermoplastic. This data is typically used to design a bottle preform for a bottle mold of a given geometry as well as the formulation which will yield the desired bottle properties.

Free-blowing a bottle from a preform involves heating the preform to a temperature above its glass transition temperature (Tg) and then expanding the preform outside of a mold so that it is free to expand without restriction until the onset of strain hardening. In articles made from a thermoplastic such as PET, the onset of strain hardening can be determined by the appearance of "pearlescence". Pearlescence is a slight hazy or "pearly" appearance caused by microcracks giving a hazy appearance with the sheen of an oyster pearl and is a term commonly used in the PET bottle industry to describe a phenomenon that occurs when the onset of strain hardening is exceeded by about 5%. Ideally, the pressure should be sufficient to cause that a very slight amount of pearlescence in the bottle.

In practice, free-blow conditions, such as heating time and blow pressure, are adjusted in a series of trial-and-error iterations so that the free-blown bottle will exhibit a slight amount of pearlescence. If the blow pressure is properly set for a PET preform, it will continue to expand until all of the PET is oriented to the point that stretching will stop at about the natural stretch ratio, or slightly beyond. For example, the optimum pressure for PET may be determined by starting with a relatively low pressure and going up in small increments until a slight amount of pearlescence occurs, then backing off slightly. Once that pressure is determined, it is held constant for all subsequent testing.

Conventional free-blowing processes for preforms made from polymers containing PEN, copolymers of PEN, and blends of PEN and PET have been found to be unsatisfactory and more difficult. Such materials can have much higher stretch ratios than PET, causing free-blown bottles from PEN/PET blends to be much bigger and thus have thinner sidewalls. Moreover, when free-blowing PEN containing copolymers and/or blends, the elevated pressure needed to start the expansion is often too high for the remainder of the free-blowing process. This excess pressure causes the expansion to exceed the natural stretch ratio by a significant amount which is evident by the amount of pearlescence in the free-blown bottle or, in extreme cases, bursting of the bottle.

U.S. Pat. No. 4,090,394 entitled "PLASTIC BOTTLE TESTING" issued on May 23, 1978 discloses a method and apparatus for producing a stress-strain type curve for evaluating the functionality of a thermoplastic bottle. The process uses a piston and an incompressible fluid to pressurize the bottle and graphically recording the movement of the driven piston and the pressure of the fluid in the bottle.

U.S. Pat. No. 4,139,586 entitled "METHOD OF FORMING ARTICLES FROM THERMOPLASTIC SHEET BY FREE-BLOWING" issued on Feb. 13, 1979 discloses a method of vacuum forming thermoplastic sheet material using a mold where a pressure differential on either side of the sheeting is formed to effect free-blowing of the molded article.

U.S. Pat. No. 5,365,792 entitled "METHOD OF DETERMINING STRETCH CHARACTERISTICS OF THERMOPLASTIC ARTICLES" issued Nov. 22, 1994 discloses a method and apparatus for determining the stretching characteristics of a thermoplastic article, such as a bottle preform, by heating the preform to at least its glass transition temperature and stretching the bottle preform using air pressure to the onset of strain hardening then correlating the stretched dimension with the selected physical property.

The above methods and apparatus have proven to be unsatisfactory since they provide inadequate information for purposes of evaluating the functionality of PEN containing thermoplastic bottles. Thus, there is a need in the art for providing a rapid means of determining the functionality of a thermoplastic container and especially for biaxially oriented thermoplastic bottles containing PEN.

SUMMARY OF THE INVENTION

Broadly, the present invention provides a method for determining the natural stretch ratio of a thermoplastic polymer composition and more specifically, a thermoplastic polymer composition containing PEN. The method includes the steps of heating a bottle preform of the polymer composition to a substantially uniform temperature followed by expanding the heated polymer by injecting a pressurized gas into the preform. During at least a portion of the expansion step, the pressure of the gas is varied inversely relative to the increase in the preform volume. In this manner, the heated preform is subjected to the greatest pressure at the beginning of the expansion step, and a desired lower pressure at the end of the expansion step.

Another aspect of the invention is an apparatus for determining the NSR of a polymer composition by free-blowing a bottle preform made from the polymer composition. The apparatus includes a means for heating the polymer preform to a substantially uniform temperature of at least its thermoplastic glass transition temperature and a means for expanding the polymer composition using a pressure that is varied inversely relative to the expansion or increase in volume of the preform.

It is an object of the present invention to provide a method for determining the expansion characteristics of a polymer composition. It is another object of the invention to provide a method for determining expansion characteristics of a bottle preform made from a polymer comprising PEN.

Another object of the invention is to provide an apparatus for determining the NSR of a polymer composition by free-blowing a heated preform of the polymer composition using a pressure that is varied inversely relative to the expansion of the preform container at least during a portion of the expansion.

These and other objects and advantages of the present invention will be readily apparent when considered with reference to the following drawing and specification.

DETAILED DESCRIPTION OF THE INVENTION

Figure 1:
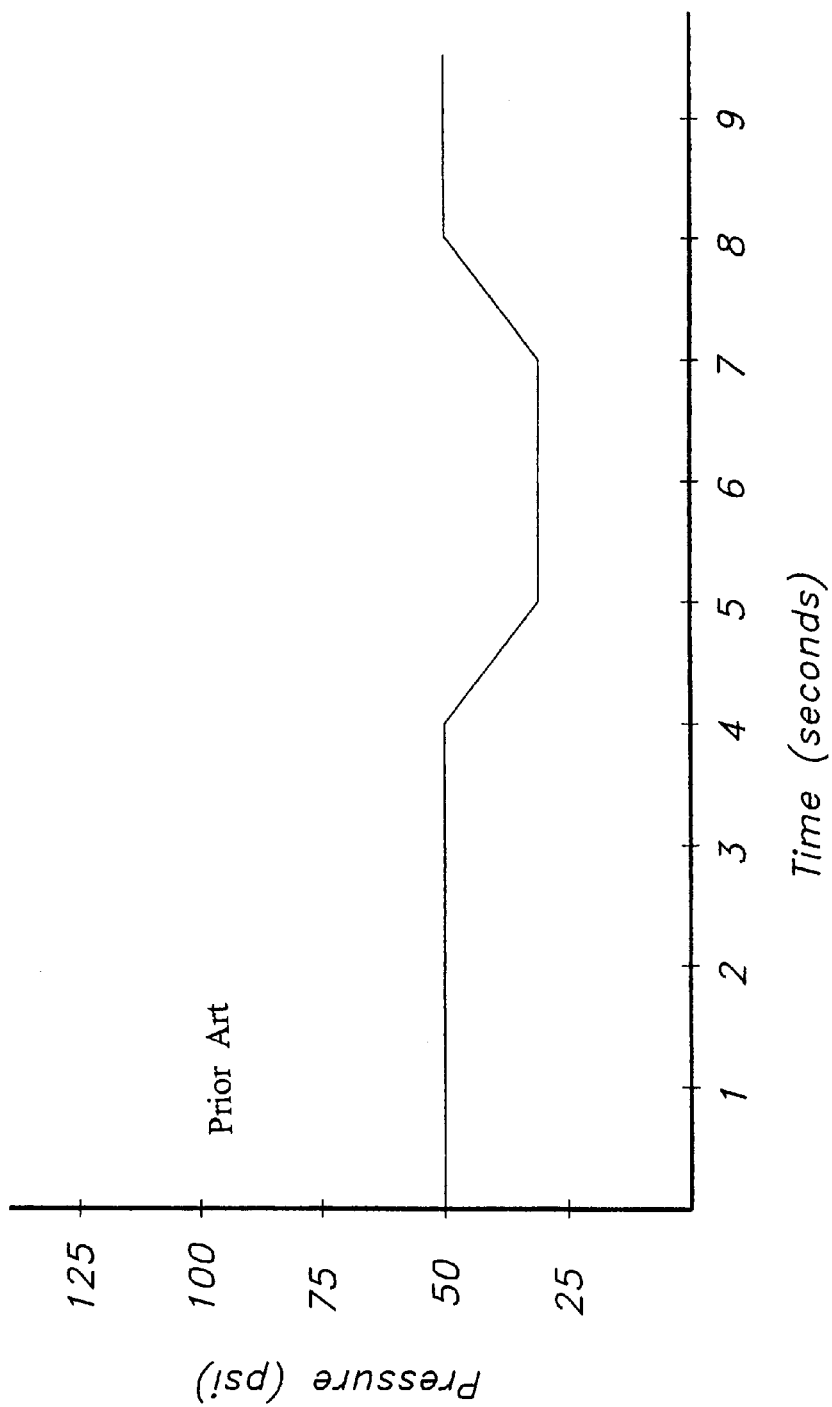
FIG. 1 is a graph of pressure vs. time of a conventional free-blow process at 50 psi.

Whenever a new polymer composition is developed (such as PET/PEN blends or PEN copolymers) new preforms must be designed to insure that the polymer in any commercially blow molded bottles will be fully oriented and thus, have optimum package properties such as tensile strength, optical and gas barrier properties. The present invention relates to an improved process for obtaining empirical data needed for designing preforms using free-blow techniques and particularly, preforms formed from polymers comprising PEN.

In accordance with this invention there is provided a method for determining the NSR of a polymer composition. In a broad sense, the present invention may be used in connection with articles such as sheet material, film and fibers as well as bottles. In such cases the film or sheet material may be unilaterally or bilaterally stretched, and fibers may be unilaterally stretched for determining natural stretch ratio. In one aspect, the present invention relates to a process for determining the NSR of a polymer composition by free-blowing a bottle preform of the composition. During at least a portion of the free-blowing process, the pressure is varied inversely relative to the increase in preform volume. Surprisingly, the process of the present invention easily and accurately produces free-blown bottles at or substantially near their NSR. Specifically, the method of the present invention comprises heating a preform of the polymer composition to a substantially uniform temperature of at least its glass transition temperature and expanding the polymer composition to about its NSR by injecting a pressurized gas into the preform so that during a portion of the expansion the pressure of the gas is inversely varied relative to the expansion of the preform container.

Polymers which benefit from the free-blowing process of the present desirably have a planar stretch ratio greater than about 12. In the case of biaxial orientation of stretch blown thermoplastic bottles, the planar stretch ratio is defined as A2/A1, where A2 is the area of stretched surface at the onset of pearlescence and A1 is the area of the original unstretched surface. Examples of suitable polymers which may benefit from the present invention include PEN containing homopolymers, copolymers and blends. Preferred polymers have from 0 to 100 weight percent PET and from 100 to 0 weight percent PEN. More preferably, the polymers have from about 50 weight percent to about 90 weight percent PET and from about 50 weight percent to about 10 weight percent PEN. Polymer, copolymers and blends of other thermoplastic compositions may also benefit from the present invention. Desirably the polymers are selected from polyesters comprising an acid component comprising repeat units from naphthalene dicarboxylic acid and a glycol component comprising repeat units from at least about 80 mole percent ethylene glycol, based on 100 mole percent dicarboxylic acid and 100 mole percent diol.

It should be understood that use of the corresponding acid anhydrides and acid chlorides of the acids is included in the term "acid form of the polyester".

The dicarboxylic acid component of the polyester may optionally be modified with one or more different dicarboxylic acids. The amount of additional dicarboxylic acid may vary widely from 0–95 mole % or greater. Such additional dicarboxylic acids include aromatic dicarboxylic acids preferably having 8 to 14 carbon atoms, aliphatic dicarboxylic acids preferably having 4 to 12 carbon atoms, or cycloaliphatic dicarboxylic acids preferably having 8 to 12 carbon atoms. Examples of additional dicarboxylic acids are: terephthalic acid, phthalic acid, isophthalic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. Polyesters may be prepared from two or more of the above dicarboxylic acids. Preferably the dicarboxylic acid component comprises up to about 80 mole % naphthalene-2,6-dicarboxylic acid and/or terephthalic acid.

In addition, the glycol component, may optionally be modified with up to about 15 mole percent, of one or more different diols other than ethylene glycol. Such additional diols include cycloaliphatic diols preferably having 6 to 20 carbon atoms or aliphatic diols preferably having 3 to 20 carbon atoms. Examples of such diols to be included with ethylene glycol are: diethylene glycol, triethylene glycol, 1,4-cyclohexanedimethanol, propane-1,3-diol, butane-1,4-diol, pentane-1,5-diol, hexane-1,6-diol, 3-methylpentanediol-(2,4), 2-methylpentanediol-(1,4), 2,2,4-trimethylpentane-diol-(1,3), 2-ethylhexanediol-(1,3), 2,2-diethylpropane-diol-(1,3), hexanediol-(1,3), 1,4-di-(hydroxyethoxy)-benzene, 2,2-bis-(4-hydroxycyclohexyl)- propane, 2,4-dihydroxy-1,1,3,3-tetramethyl-cyclobutane, 2,2-bis-(3-hydroxyethoxyphenyl)-propane, and 2,2-bis-(4-hydroxypropoxy-phenyl)-propane. Polyesters may also be prepared from two or more of the above diols.

The PEN containing polymer may also contain small amounts of trifunctional or tetrafunctional comonomers such as trimellitic anhydride, trimethylolpropane, pyromellitic dianhydride, pentaerythritol, and other polyester forming polyacids or polyols generally known in the art. Other ingredients can be added to the compositions of the present invention to enhance the performance properties of the polymers. For example, crystallization aids, impact modifiers, surface lubricants, denesting agents, stabilizers, antioxidants, ultraviolet light absorbing agents, metal deactivators, colorants, nucleating agents, stabilizers, fillers, reheat enhancing aids and the like, can be included herein. All of these additives and the use thereof are well known in the art and do not require extensive discussions.

The PET and PEN based polyesters of the present invention can be prepared by conventional polycondensation procedures well known in the art. Such processes include direct condensation of the dicarboxylic acid(s) with the diol(s). The polyesters may also be subjected to solid state polymerization methods.

Heating of the thermoplastic preform can be accomplished using any method that desirably, will give a uniform temperature profile across the dimensions of the preform. For example, the preform may be heated by convection, circulating hot air across the surface of the preform and the like.

The preform may also be heated using electromagnetic radiation such as infrared radiation. During heating, using infrared radiation, a temperature distribution across the preform may be irregular in the direction of the thickness of the preform so that the side irradiated heats more rapidly than the opposite side. The temperature distribution and temperature rise are affected by the infrared radiation absorption and transmission factors of the polymer composition, the thickness of the preform, the amount of radiant energy emitted, conduction of heat through the polyer composition and the heating time.

The preform may also be heated using a liquid medium that provides a uniform temperature distribution and conduction to the thermoplastic preform. The polymer composition should be substantially insoluble in the heating liquid. In the case of PET and PEN, a variety of liquids or mixtures of liquids may be used, such as water, some hydrocarbons, alcohols, ketones, and esters. For example, suitable liquids include 2-butanol, isobutyl alcohol, n-propyl alcohol, diethyl ketone, methyl propyl ketone, methyl isobutyl ketone, n-heptane, methyl cyclohexane, and propyl acetate. Since the preform temperature has a large effect on the polymer expansion, it is important that the method of heating be uniform.

If a liquid other than water is used, the liquid should boil at a temperature of at least the polymer glass transition temperature (Tg) to soften the polymer preform enough for the preform to be free-blown. The Tg of PET is about 80° C. However, the combination of temperature and heat transfer coefficient should be such that the inside surface of the preform would reach Tg prior to the outside surface crystallizing, if the preform is heated from the outside with the liquid. Obviously, heating may be done from the inside by filling the preform with the liquid, or by a combination of inside/outside heating. The Tg of the thermoplastic article should be attained across the article's thickness, and in the case of a bottle preform, the Tg must be reached across the wall thickness.

In accordance with the invention, an inert gas and desirably high pressure air, is used to begin expansion of the heated thermoplastic preform. Other suitable inert gases may be used for the expansion of the heated preform, as will be apparent to those skilled in the art. During expansion, the expansion air pressure is varied inversely, i.e., it is reduced until the tensile strength of the free-blown bottle sidewall is greater than the stress caused by air pressure inside the free-blown bottle. At the beginning of the free-blowing process, high pressure air is utilized to start the inflation. For example, in a typical 2-liter soft drink preform, suitable initial pressures are typically greater than about 100 psi and preferably between about 100 and about 200 psi. Once the heated preform begins to inflate, the air pressure is reduced so that the increasing stress in the inflating preform sidewall is controlled. In accordance with the invention, the air pressure is allowed to decrease inversely relative to the expansion or increase of the preform volume. In a preferred embodiment, the air pressure is reduced to a final pressure of about 40 psi to about 60 psi which is then held constant for the remainder of the preform expansion. As the preform inflates, the polyester orients and the tensile strength of the sidewall increases. Advantageously, at or near the NSR of the polyester, the sidewalls display their maximum tensile strength. In the process of the present invention the pressure is allowed to decrease in such a way that when the tensile strength reaches its maximum, it exceeds the stress caused by the pressurized air, the preform stops expanding.

In the case of fibers, films and sheeting, stretching may be accomplished by means known to those skilled in the art. For example, pairs of driven nip rolls, operated at selected different speeds may be used. In the case of fibers, films and sheeting, dimensions may be measured initially, i.e., before heating while the article is at a selected temperature in the solid state, and then measured at the onset of strain hardening.

The strain rate is primarily a function of the blow pressure, the size of the orifice through which the blow air is introduced and the temperature of the preform. However, because the thickness of the expanding preform changes due to the stretching, the strain rate is not constant during the free-blowing process. The equation for hoop stress in a preform's sidewall is: $S=Pr/t$, where $P$=pressure, $r$=preform's radius and $t$=thickness of preform sidewall.

It was surprising that the process of the present invention could readily mimic the conditions of a commercial reheat blow-molding machine to produce bottles, which are stretched to or near their NSR. It was also surprising that conventional procedures which use a constant high pressure to inflate the preform were tried and did not yield suitable polymer characteristic information.

Figure 2:
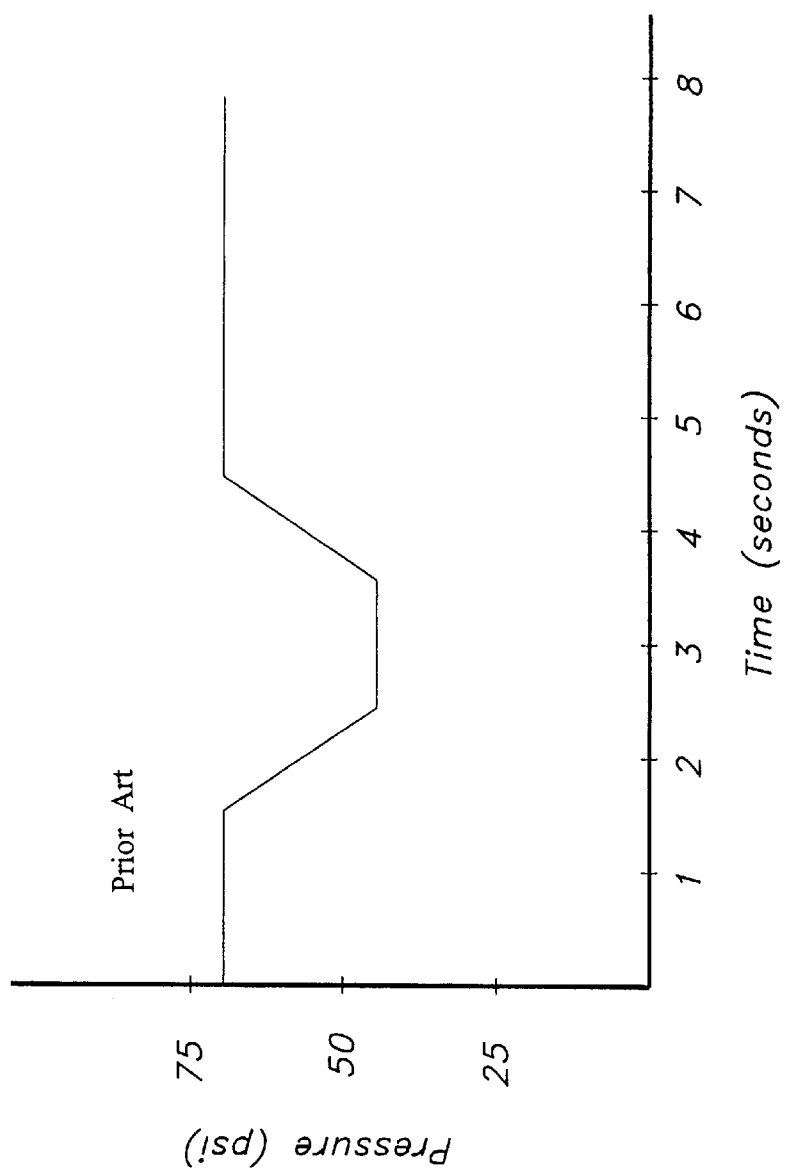
FIG. 2 is a graph of pressure vs. time of a conventional free-blow process at 70 psi.

Commercial blow molding equipment utilizes relatively high inflation rates. In a commercial setting a preform is blown out against a mold to make a container such as a bottle. Because bottles are blown against a mold, over inflation is generally not a problem when appropriately designed preforms are blown into commercial bottles. Doing free-blow studies using a slow rate will not yield stretch ratios that are typical of those in a commercial bottle-blowing machine. For example, referring to FIGS. 1 and 2, low blow pressure failed to provide desirable free-blow bottles. Blow pressures at or less than about 50 psi were barely sufficient to overcome the tensile strength at yield of the preform. This resulted in undesirably long blowing times, i.e., the time necessary to initiate inflation (4 seconds) and the inflation time (4 seconds). The slower the preform is inflated, the more it will stretch. Thus, free-blown bottles blown with lower blow pressures display artificially high hoop and axial stretch ratios which are not suitable for designing preforms for commercial blow molding machines.

Figure 3:
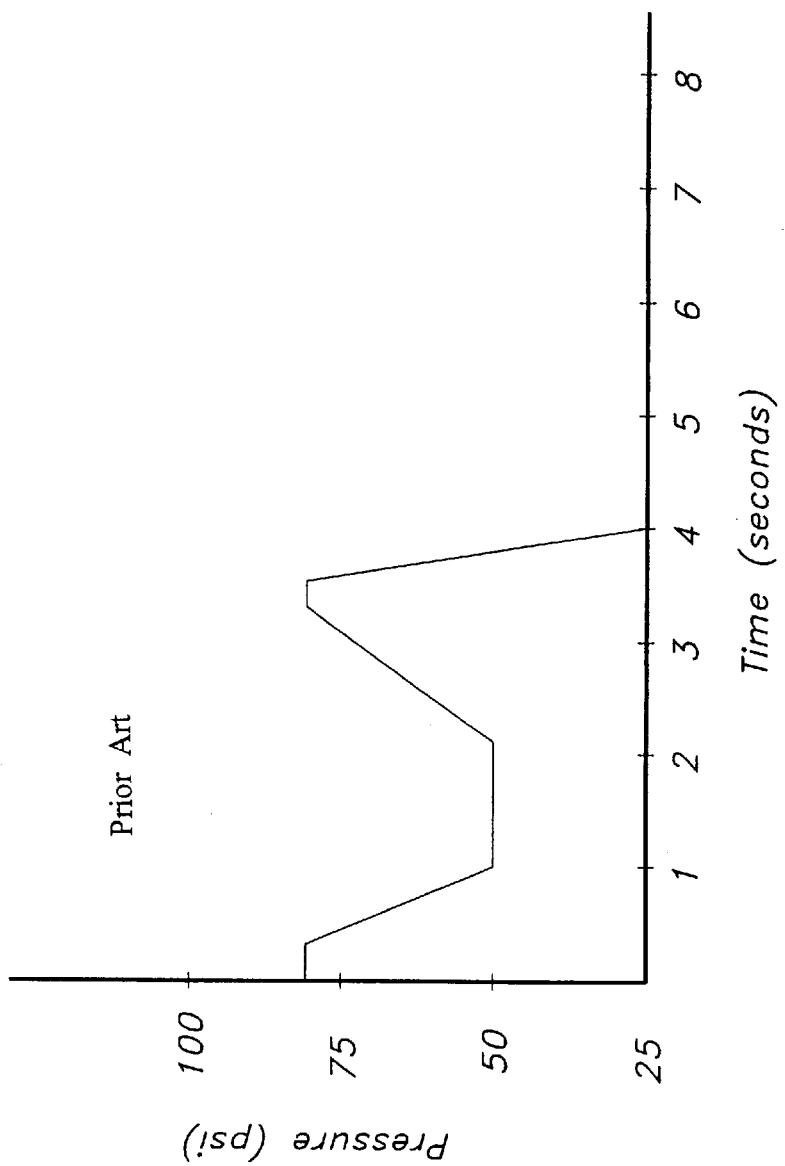
FIG. 3 is a graph of pressure vs. time of a conventional free-blow process at 80 psi.

To get a good correlation, the free-blown bottles need to be blown at a fast rate. As previously discussed, free-blowing at a fast rate requires a high pressure, and a high pressure typically causes the NSR to be exceeded by a great amount, often bursting the bottle. For example, using a constant blow pressure, when the blow pressure was increased above about 70 psi, the preform expanded out past the NSR yielding hoop and axial measurements which were too great, and were unacceptable for calculating stretch ratios. Free-blow bottles blown at high blow pressures showed unacceptable pearlescence or bursting during blowing which evidenced that the NSR was greatly exceeded during inflation. FIG. 3 depicts a pressure vs. time plot for a bottle free-blown at 80 psi while the inflation rate was relatively fast (as desired), the bottle developed extreme pearlescence and then burst as is indicated by the precipitous drop in pressure after three seconds.

Figure 4:
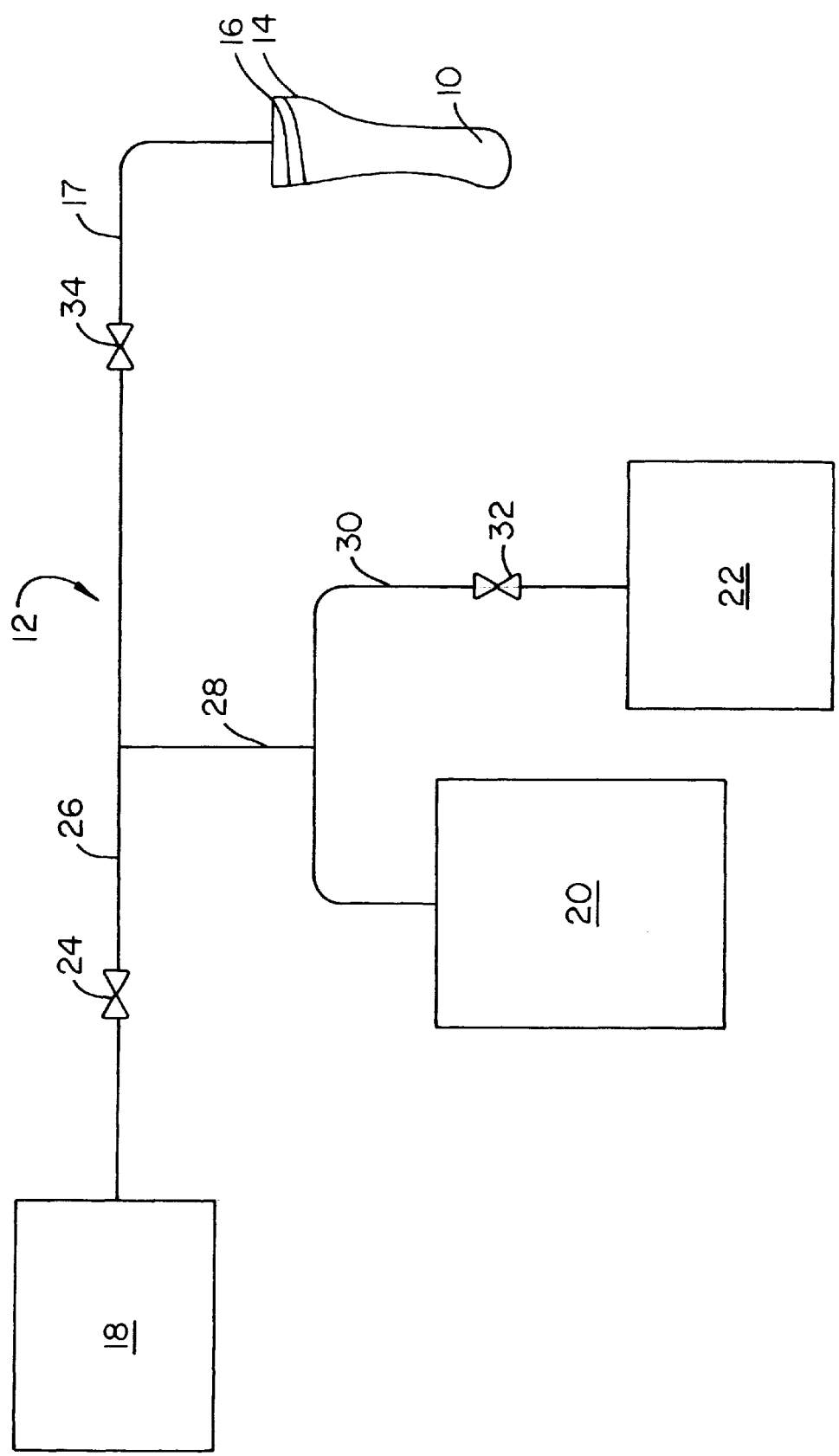
FIG. 4 is a schematic showing an apparatus suitable for an embodiment of the present invention.

The present invention further relates to an apparatus for varying the pressure during expansion of a hot bottle polymer preform so that the free-blowing process begins at a high pressure and decreases as the preform expands. Using a 2 liter bottle preform for illustration and referring to FIG. 4, an apparatus is schematically illustrated which is suitable for the practice of the present invention. Referring more particularly to the drawing, a thermoplastic preform 10 is heated, using any of the aforementioned methods, and affixed to a pressurized air source 12. One skilled in the art will understand that the preform 10 may be heated either prior to being affixed to the pressurized air source 12 or afterwards without affecting the scope and spirit of the invention described herein. Thermoplastic preforms 10 are well known in the art and are adapted to be detachably affixed to the pressurized air source 12 by a neck portion 14 having threads 16 which allow the thermoplastic preform 10 to be screwed onto a mating portion of the inflation line 17. It is understood by those skilled in the art that other means for detachably affixing the thermoplastic preform to the pressurized air source may be used. For example, the thermoplastic preform may be affixed to a first member which in turn is detachably mated to a second member affixed to the pressurized air source. Another means by which the preform may be detachably affixed to the pressurized air source 12 includes clamping the neck portion 14 of the preform during inflation.

The pressurized air source 12 includes a constant pressure, high pressure air source 18; a constant volume air source 20, such as, an air tank or other non-expanding vessel; and, in a preferred embodiment, a constant pressure, low pressure air source 22. The high pressure air source 18 is connected to an isolation valve 24 which in turn is connected to the blow line 26. The constant volume air source 20 is connected to the blow line 26 via air flow line 28 and desirably, is associated with the constant pressure, low pressure air source 22 by air flow line 30. Isolation valve 32 is connected to the air flow line 30. It separates the low pressure air source 22 from the high pressure air source 18 and the constant volume air source 20 when the air pressure in the blow line 26 is greater than the air pressure in the low pressure air source 22. The blow line 26, which may optionally have a pressure gauge (not shown) connected to it, is connected to isolation valve 34. The preform isolation valve 34 may also be used to control the air flow through the inflation line 17 to the preform 10.

Desirably, the high pressure air source 18 has a pressure greater than about 80 psi, preferably it is from about 100 psi to about 200 psi and more preferably it is from about 100 psi to about 150 psi. Desirably, the low pressure air source 22 has a pressure less than 80 psi, preferably it is less than about 75 psi and more preferably it is from about 40 psi to about 70 psi.

The apparatus of the present invention is prepared for use by closing the preform isolation valve 34 and opening valve 24. High pressure air is charged to the constant volume air source 20 using the blow line 26 and the air flow line 28. When the constant volume air source 20 is filled to the desired pressure, isolation valve 24 is closed. Note that valve 32 is a one-way valve which allows air to flow only away from low pressure air source 22.

In operation, the preform 10 is desirably uniformly heated to at least it glass transition temperature. When the heated preform 10 is ready to be free-blown, the preform isolation valve 34 is opened. Air from the constant volume air source 20 flows through lines 28, 12 and 17 and inflates the hot preform 10. Since the constant volume air source 20 has a fixed volume, the blow line pressure decreases as the preform 10 expands. The pressure at any given time can be determined using the gas law $(P_1)X(V_1)=(P_2)X(V_2)$.

Figure 5:
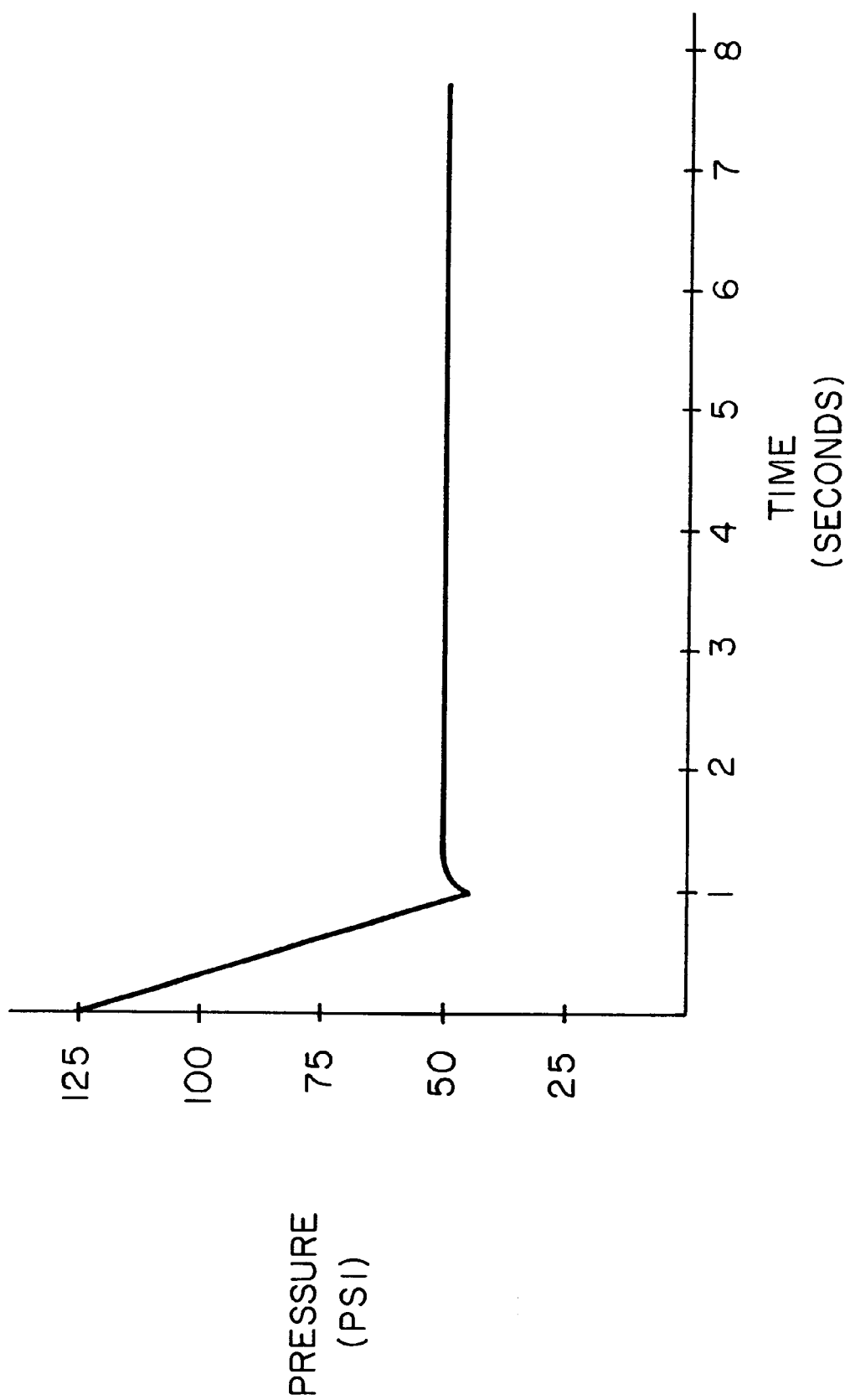
FIG. 5 is a graph of pressure vs. time of the free-blow process of the present invention.

The apparatus of the present invention provides an initial pressure which is sufficient to initiate rapid inflation but immediately starts to drop after the onset of the preform 10 expansion. In a preferred embodiment of the apparatus of the present invention, the air pressure in the constant volume air source 20 is insufficient to completely inflate the preform 10, and additional air is introduced via low pressure air source 22 through isolation valve 32 and line 30 to complete the preform expansion process. The preform 10 is allowed to cool below its Tg while still under pressure. FIG. 5 depicts a time-pressure chart of this preferred embodiment.

Desirably, the volume of air charged to the constant volume source 20 may be adjusted as necessary via a fill/drain line (not shown) using conventional means such as the addition or removal of a substantially non-compressible fluid, such as water or oil.

As an example, a limited number of combinations of $P_1$ and $V_1$ were tried to evaluate the constant volume air source 20 and what effect these two variables would have on the hoop and axial stretch ratios. The pressure for a given tank volume 20 was determined by doing the following:

With a cool (room temperature) free-blown bottle in place of a preform in the free-blow apparatus, determine what initial surge tank pressure would result in a final hoop stress of about 7,800 psi. This calculation was made using the previously mentioned hoop stress equation: S=Pr/t. When the level of stress in the preform significantly exceeded 7,800 psi, excessive pearlescence was typically observed.

Below is a tabulation of some combinations of tank volumes 20 and initial tank pressures that were tried when free-blowing one-half liter preforms made from a blend with 15 mole percent PEN and 85 mole percent PET:

TABLE 1

| Initial Tank Vol. | Tank Pres. | I.P.S. | F.P.S. | Hoop S.R. | Axial S.R. |
|---|---|---|---|---|---|
| 865 cc | 133 psi | 238 psi | 7,790 psi | 4.55:1 | 2.98:1 |
| 715 cc | 150 psi | 259 psi | 7,790 psi | 4.53:1 | 2.98:1 |
| 565 cc | 181 psi | 291 psi | 7,790 psi | 4.58:1 | 2.99:1 |

I.P.S. = Calculated initial preform stress (at start of blowing).
F.P.S. = Calculated final preform stress (at end of blowing).

It was found that bottle could be free-blown to the NSR using various combinations of initial pressures and tank volumes. Furthermore, for a particular combination of tank volume and pressure, the resulting NSRs were generally consistent. The above data further indicates that the hoop and axial stretch ratios are not a function of the air tank volume and its initial pressure in those ranges.

COMPARATIVE EXAMPLES 1–4

In Examples 1–4 preform measurements were made using the prior art, constant pressure technique. The apparatus used in these examples had only a regulated high pressure air supply source and a means for affixing the hot preform to the blow line. The preforms were heated to a temperature of about 115° C. prior to initiating free-blowing. Other conditions were set as indicated in Table 2 below. The results are in Table 2 below:

TABLE 2

| Example | Pressure | Axial S.R. | Hoop S.R. | Planar S.R. |
|---|---|---|---|---|
| 1 | 40 | 3.37:1 | 5.35:1 | 18.0:1 |
| 2 | 50 | 3.34:1 | 5.32:1 | 17.8:1 |
| 3 | 60 | 3.38:1 | 5.33:1 | 18.0:1 |
| 4 | 70 | 3.49:1 | 5.38:1 | 18.8:1 |

SR = Stretch Ratio
Axial = up and down the preform and bottle
Hoop = the diameter of the preform and bottle
Planar SR = Axial X Hoop

EXAMPLE 5

In accordance with the present invention, the preform was heated to a temperature of about 115° C. prior to initiating free-blowing. Using the apparatus and a preferred method in accordance with the invention, the initial tank pressure was changed to 150 psi which gave an initial pressure on the preform of 118 psi. A secondary pressure source of 50 psi was available and used to complete the preform expansion, if so needed. The results are in Table 3 below:

TABLE 3

| Example | Pressure | Axial SR | Hoop SR | Planar SR |
|---|---|---|---|---|
| 5 | — | 2.73:1 | 4.38:1 | 12.0:1 |

It is readily apparent from Examples 1–4 and Example 5, the Planar stretch ratio yielded using the method and apparatus of the present invention is significantly less than what is achieved using conventional techniques. Use of the present invention greatly improves the design of a polymer preform by yielding stretch ratios that are representative of the polymer characteristics.

Although the present invention has been described in terms of the presently preferred embodiment, it is to be understood that such disclosure is not to be interpreted as limiting to the invention described herein. No doubt that after reading the disclosure, various alterations and modifications will become apparent to those skilled in the art to which the invention pertains. It is intended that the appended claims be interpreted as covering all such alterations and modifications as fall within the spirit and scope of the invention.

I claim:

1. A method for determining the natural stretch ratio (NSR) of a polymer composition comprising the steps of:
    a) heating a bottle preform of said polymer composition to a substantially uniform temperature of at least its glass transition temperature; and
    b) expanding said heated preform to about the NSR of the polymer composition by injecting a pressurized gas into said preform, wherein the pressure of said expansion gas is decreased during at least a portion of said expansion.

2. The method of claim 1 wherein said polymer composition is selected from the group consisting of PET, PEN, copolymers and blends thereof.

3. The method of claim 1 wherein said polymer composition has a planar stretch ratio greater than about 12.

4. An apparatus for determining the natural stretch ratio for a polymer composition by free-blowing a bottle preform of the polymer composition heated to at least its glass transition temperature, said apparatus comprising:
    a) a blow line;
    b) means for securing said preform to said blow line; and
    c) means for inflating said preform through said blow line using a fluid pressure that is inversely related to the increase in volume of said polymer composition container during at least a portion of said inflation.

5. The method of claim 1 wherein said polymer composition is heated by contacting said preform with a non-soluble thermal transfer medium at a uniform temperature.

6. The method of claim 1 wherein said polymer composition is heated using infrared radiation.

7. A method for determining NSR of a polymer composition selected from the group consisting of PET, PEN, copolymers and mixtures thereof comprising the steps of:
    a) heating a bottle preform of said polymer composition to a substantially uniform temperature of at least its glass transition temperature; and
    b) expanding said preform by injecting a pressurized gas into said heated preform wherein the pressure of said expansion gas is inversely related to said preform expansion.

8. The method of claim 7 wherein said preform is expanded by free-blowing.

9. The method of claim 7 wherein said preform is heated by contacting said container with a non-soluble thermal transfer medium selected from the group consisting of water, alcohols, ketones, esters and mixtures thereof.

10. The method of claim 9 wherein said thermal transfer medium is selected from the group consisting of 2-butanol, isobutyl alcohol, a-propyl alcohol, diethyl ketone, methyl propyl ketone, n-heptane, methyl cyclohexane, propyl acetate and mixtures thereof.

11. The method of claim 7 wherein said gas is air.

12. The method of claim 7 wherein said polymer composition has a planar stretch ratio greater than about 12.

13. The method of claim 7 wherein said polymer composition has from 0 to 100 weight percent PET and from 100 to 0 weight percent PEN.

14. The method of claim 7 wherein said polymer composition has from about 50 to about 90 weight percent PET and from about 50 to about 10 weight percent PEN.

15. The apparatus of claim 4 wherein said preform is removably affixed to said blow line.

16. The apparatus of claim 4 wherein said fluid is an inert fluid.

17. The apparatus of claim 16 wherein said inert fluid is air.

18. The apparatus of claim 17 wherein said inflating means comprises;
    1) a first constant pressure air source;
    2) a constant volume air source; and
    3) a first isolation means between said constant pressure air source and said constant volume air source for pressurizing said constant volume air source from said constant pressure air source and isolating the same when said constant volume air source has a predetermined pressure.

19. The apparatus of claim 18 wherein said first constant pressure air source has a pressure greater than about 100 psi.

20. The apparatus of claim 18 wherein said inflating means further comprises:

4) a second isolation means on said blow line for isolating said heated preform from said pressurized constant volume air source prior to said preform being inflated; and 5) a second constant pressure air source associated with said blow line having a pressure less than said first constant pressure air source.

21. The apparatus of claim 20 wherein said second constant pressure air source has a pressure of from about 40 psi to about 70 psi whereby said second constant pressure air source is adapted to be used if the pressure in said constant volume air source is insufficient to expand said thermoplastic container to its NSR.

* * * * *